US00PP12268P2

(12) United States Plant Patent
Olesen et al.

(10) Patent No.: US PP12,268 P2
(45) Date of Patent: Dec. 11, 2001

(54) HYBRID TEA ROSE VARIETY 'POULEN002'

(75) Inventors: L. Pernille Olesen; Mogens N. Olesen, both of Fredensborg (DK)

(73) Assignee: Poulsen Roser APS, Fredensborg (DK)

( * ) Notice: Subject to any disclaimer, the term of this patent is extended or adjusted under 35 U.S.C. 154(b) by 0 days.

(21) Appl. No.: 09/276,889

(22) Filed: Mar. 25, 1999

(51) Int. Cl.[7] ..... A01H 5/00
(52) U.S. Cl. ..... Plt./134
(58) Field of Search ..... Plt./134, 130

*Primary Examiner*—Howard J. Locker

(57) ABSTRACT

A new hybrid tea rose plant which has abundant, large, fragrant amber-yellow flowers and attractive foliage. This new and distinct variety has shown to be uniform and stable in the resulting generations from asexual propagation.

2 Drawing Sheets

SUMMARY OF THE INVENTION

The present invention constitutes a new and distinct variety of a hybrid tea rose plant which originated from a controlled crossing between two unnamed, non-commercial seedlings. The two parents were crossed and the resulting seeds were planted in a controlled environment. The new variety is named 'POULen002'.

The new rose may be distinguished from its seed parent, an unnamed seedling, created by the same inventors, by the following combination of characteristics:

1. The seed parent is classified as a floribunda rose, while 'POULen002' is a hybrid tea;
2. The seed parent's blooms are a clear yellow color; whereas, 'POULen002' has amber yellow blooms;
3. The seed parent blooms are smaller in size and have fewer petals than 'POULen002'.

The new variety may be distinguished from its pollen parent, an unnamed seedling created by the same inventors, by the following combination of characteristics:

1. The seed parent has ivory-yellow blooms; whereas, 'POULen002' has amber-yellow blooms;
2. The petalage of the pollen parent is double; whereas, 'POULen002' has very double petalage;
3. The fragrance of 'POULen002' is much more intense than the fragrance of the pollen parent.

The objective of the hybridization of this rose variety for commercial greenhouse cuture was to create a new and distinct variety with unique qualities, such as:

1. Uniform and abundant flowers;
2. Vigorous and compact growth;
3. Fragrance;
4. Large, quartered blooms;
5. Disease resistance.

This combination of qualities is not present in previously available commercial cultivars of this type and distinguishes 'POULen002' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULen002' was selected by the inventors in spring, 1989 as a single plant from the progeny of the aforementioned hybridization.

Asexual reproduction of 'POULen002' by traditional budding was first done by L. Pernille and Mogens N. Olesen in their nursery in Fredensborg, Denmark in August 1989. This initial and other subsequent propagations conducted in controlled environments have demonstrated that the characteristics of 'POULen002' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULen002'. Specifically illustrated in SHEET 1:

1. Stem showing branching and the attachment of leaves, buds, and peduncles;
2. Flower bud, partially opened bud, and open bloom;
3. Flower petals, detached;

Specifically illustrated in SHEET 2:

4. Sepals, receptacle, and pedicel;
5. Flowering stem as well as a bare stem exhibiting thorns;
6. Leaves.

DETAILED DESCRIPTION OF THE VARIETY

The following is a description of 'POULen002', as observed in a field nursery in Jackson County, Oreg. in August 1998. Color references are made using The Royal Horticultural Society (London, England) Colour Chart, 1995, except where common terms of color are used.

For a comparison, several physical characteristics of the rose variety 'POULari', a hybrid tea rose variety from the same inventors described and illustrated in U.S. Plant Pat. No. 9,274 and issued on Sep. 5, 1995 are compared to 'POULen002' in Chart 1.

CHART 1

| | 'POULen002' | 'POULari' |
|---|---|---|
| Size of open bloom. | 100–130 mm. | 120–140 mm. |
| Color of upper surface | Yellow Group 10C-10D. | White Group 155D. |

CHART 1-continued

| | 'POULen002' | 'POULari' |
|---|---|---|
| when open. | | |
| Petalage. | Very Double; 70–90 petals. | Very Double; 55–70 petals. |

Parents:
*Seed parent.*—Unnamed seedling.
*Pollen parent.*—Unnamed seedling.
Classification:
*Botanical.*—*Rosa hybrida.*
*Commercial.*—Hybrid Tea.

FLOWER AND FLOWER BUD

Blooming habit: Nearly continuous.
Flower bud:
*Size.*—Upon opening, 50 mm in length from base of receptacle to end of bud.
*Bud form.*—Long and pointed with a high center.
*Bud color.*—As sepals unfold, Yellow-Orange Group 16B. Yellow-Orange Group 16A at ¼ opening.
*Sepals.*—Green Group 143B. Moderately foliaceous appendages on three of the five sepals. Surfaces of sepals moderately pubescent. Stipitate glands are present on the outer side of the sepal and along the margins and foliaceous appendages.
*Receptacle.*—Surface: Generally smooth with a very limited number of stipitate glands. Shape: Urn-shaped. Size: Medium. 10 mm (h)×12 mm (w). Color: Green Group 143C.
*Peduncle.*—Surface: Moderately covered with stipitate hairs. Length: 60–100 mm average length. Color: Green Group 143B with intonations of Greyed-Red Group 180A–C. Strength: Erect.
*Borne.*—Generally with 1–3 buds per flowering stem.
Flower bloom:
*Fragrance.*—Strong, with undertones of fruit, with a herbaceous overtone.
*Duration.*—As a field plant, flowers last from 4 to 7 days. As a cut flower 3 to 5 days. Petals fall cleanly away from plant.
*Size.*—Medium for a hybrid tea rose. Average flower diameter is 100–130 mm when open.
*Form.*—Cup shaped, slightly quartered.
*Shape of flower when viewed from the side.*—Upon opening, upper part: Flattened convex. Upon opening, lower part: Flattened convex. Open flower, upper part: Flattened convex. Open flower, lower part: Concave.
*Petalage.*—Very double with a range of 70–90 petals under normal conditions with 5–10 petaloids.
Color:
*Upon opening.*—Outermost petals: Upper Surface: Yellow-Orange Group 16B. Reverse Side: Yellow-Orange Group 16B. Basal portion of petal Yellow Group 12A. Innermost petals: Upper Surface: Yellow-Orange Group 15C. Reverse Side: Yellow-Orange Group 15A.
*Upon opening, basal petal spots.*—Extend into basal zone. Outermost petals: Outer Side: Yellow Group 9A. Inner Side: Yellow Group 12A. Innermost petals: Outer Side: Yellow Group 9A. Inner Side: Yellow Group 9A.
*After opening, petals.*—Outermost petals: Upper Surface: Yellow Group 10C. Reverse Side: Yellow Group 10D. Innermost petals: Marginal Zone, Upper Surface: Yellow Group 9B. Basal and middle Zone, Upper Surface: Yellow Group 9C. Marginal Zone, Reverse Side: Yellow Group 15D. Basal and middle Zone, Reverse Side: Yellow Group 9C.
*After opening, basal petal spots.*—Outermost petals: Outer Side: Yellow Group 12A. Inner Side: Yellow Group 12A. Innermost petals: Outer Side: Yellow Group 12A. Inner Side: Yellow Group 12A.
General Tonality: On open flower Yellow Group 10B–C. No change in the general tonality at the end of the fourth day. Afterwards, general tonality is Yellow Group 16D.
Petals:
*Petal reflex.*—Strong.
*Petal edge.*—With a slight indentation in center of margin.
*Shape.*—Deltoid.
*Petaloids.*—Present. Quantity: 5–10.
*Texture.*—Very thick.
*Arrangement.*—Imbricated.
Reproductive organs:
*Pollen.*—Color: Yellow-Orange Group 22A. Quantity: Limited.
*Anthers.*—Color: Yellow-Orange Group 21B. Quantity: Average.
*Filaments.*—Color: Yellow Group 9A.
*Stigmas.*—Slightly inferior in position to the anthers. Color: Yellow Group 9B.
*Styles.*—Stigmas and styles are pilose. Color: Below Stigma: Red Group 50A. Base of Stigma: Yellow-Green Group 145D.
*Hips.*—None observed.

PLANT

Plant growth: Vigorous, upright to bushy. When grown on its own roots, the average height of the plant itself is 100–120 cm and the average width is 80–90 cm.
Stems:
*Color.*—Young wood: Green Group 144A. Older wood: Green Group 144A.
*Thorns.*—Incidence: Moderate to heavy on older growth. Few thorns on new growth. Size: Average length: 10 mm. Color: Greyed-Orange Group 166C. Shape: Deeply concave.
*Surface.*—Young wood: Smooth. Older wood: Smooth.
*Length.*—35–45 cm.
Plant foliage: Normal number of leaflets on leaves in middle of the stem: 5 leaflets.
*Leaf size.*—Large. 120 mm (1)×110 mm (w).
*Abundance.*—Average.
*Color.*—Upper Leaf Surface: Yellow-Green Group 147A. Lower Leaf Surface: Yellow-Green Group 147B–C. Juvenile foliage: Upper Surface: Green Group 137A, with intonations of Greyed-Purple Group 184B–C. Lower Surface: Green Group 137B, with intonations of Greyed-Purple Group 184B–C. Anthocyanin: Location: Margins and underside of leaflets. Color: Greyed-Purple Group 184B–C.
Plant leaves and leaflets:
*Stipules.*—Size: 20 mm–25 mm. Color: Yellow-Green Group 144B. Stipitate glands: Moderate number on underside and on margins. Less abundant on top of stipules.

*Petiole.*—Length: 30 mm. Color: Green Group 144B. Underneath: With prickles. Margins: Limited number of stipitate hairs. Intonation: None in mature foliage. In juvenile foliage, and on buds and rachis tone is Greyed-Purple Group 184C–187A.

*Rachis.*—Color: Yellow-Green Group 144A. Underneath: With prickles. Margins: Limited number of stipitate hairs on upper margins.

*Leaflet.*—Edge: Serrated. Shape: Ovate. Texture: Thick, with matte finish.

Disease resistance: Average resistance to mildew, black spot, and Botrytis under normal growing conditions in Jackson County, Oreg.

Cold hardiness: 'POULen002' has been found to be cold hardy in Denmark, and in Jackson County, Oreg.

We claim:

1. A new and distinct variety of rose plant of the hybrid tea class, substantially as herein illustrated and described as a distinct and novel rose variety due to its abundant, amber-yellow flowers, vigorous and compact growth, year round flowering under glasshouse conditions, suitability for production from softwood cuttings in pots, and durable flowers and foliage which make the variety suitable for distribution in the floral industry.

* * * * *

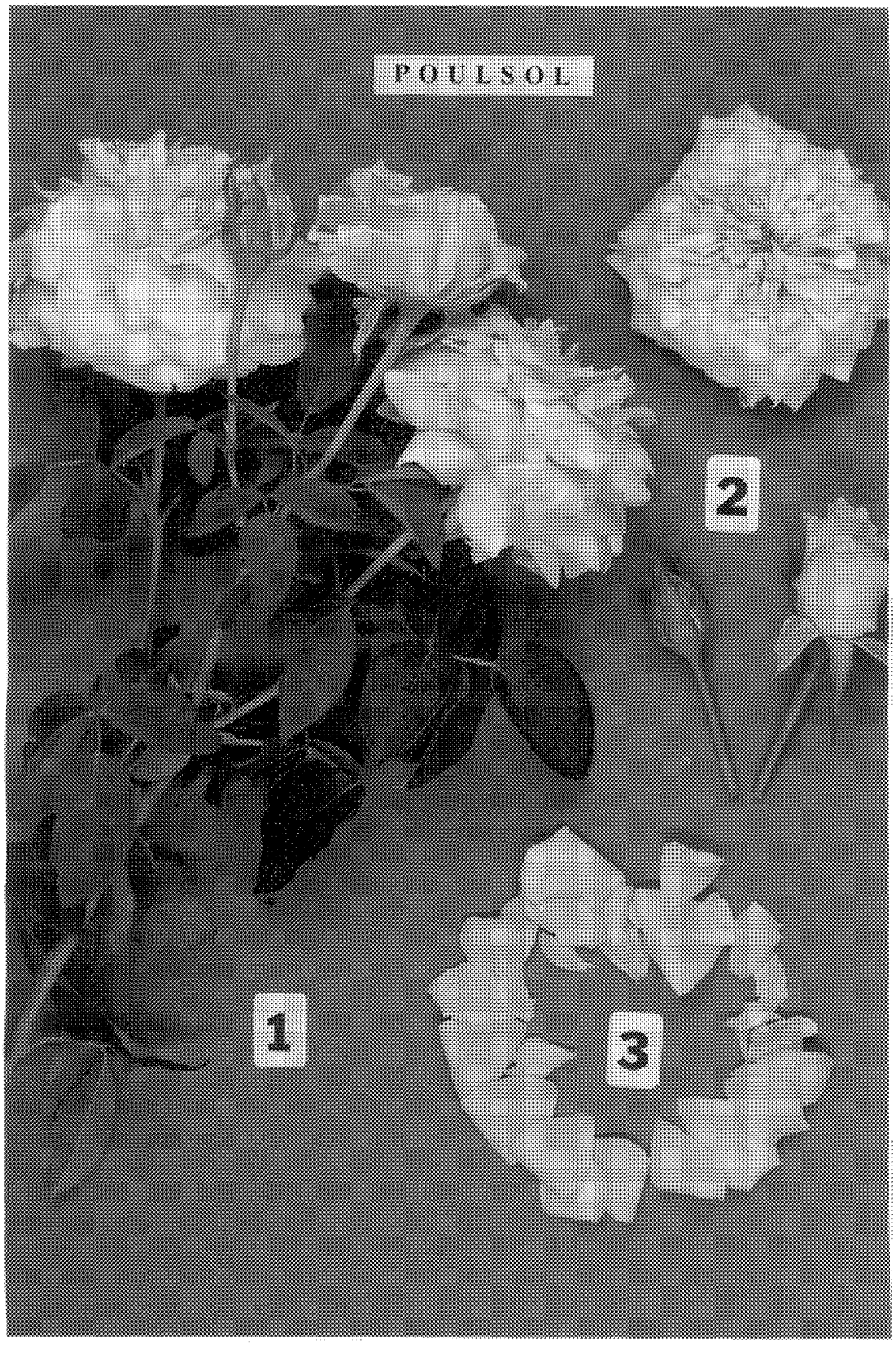
POULSOL
1
2
3

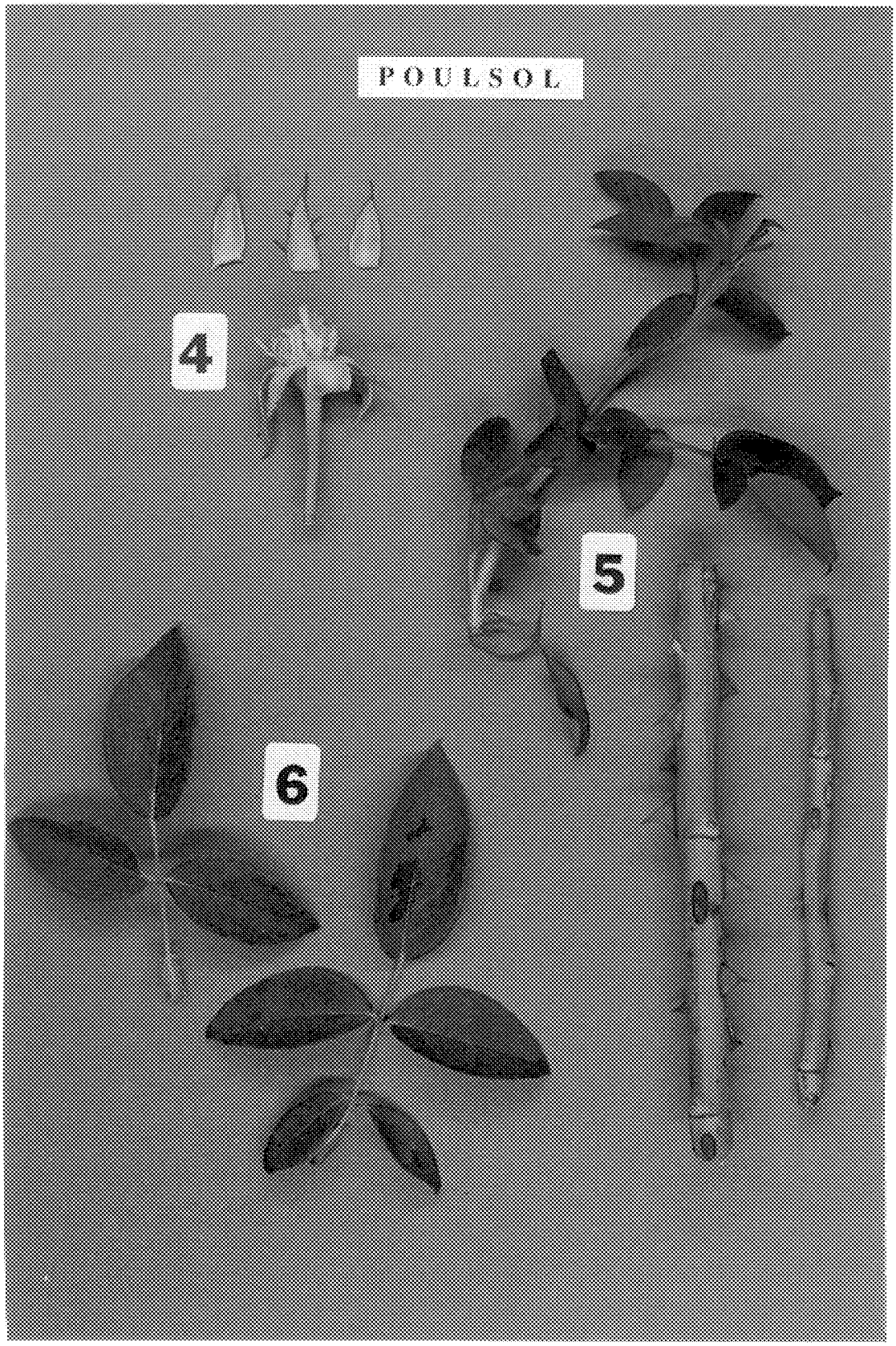
POULSOL
4
5
6